United States Patent
Collins et al.

(10) Patent No.: US 9,095,396 B2
(45) Date of Patent: *Aug. 4, 2015

(54) POROUS IMPLANT WITH NON-POROUS THREADS

(75) Inventors: Michael Scott Collins, San Marcos, CA (US); Jeffrey Bassett, Vista, CA (US); Steven Pelote, Vista, CA (US); Joseph A. Salvi, Chula Vista, CA (US); Shahram Zamani, San Diego, CA (US); Mojtaba Esfahani, Del Mar, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,831

(22) Filed: Jul. 30, 2012

(65) Prior Publication Data

US 2013/0022943 A1    Jan. 24, 2013

Related U.S. Application Data

(63) Continuation-in-part of application No. 12/167,107, filed on Jul. 2, 2008, now Pat. No. 8,231,387.

(51) Int. Cl.
*A61C 8/00*    (2006.01)

(52) U.S. Cl.
CPC ............. *A61C 8/0012* (2013.01); *A61C 8/0016* (2013.01); *A61C 8/0018* (2013.01); *A61C 8/0022* (2013.01); *A61C 8/0013* (2013.01)

(58) Field of Classification Search
CPC .. A61C 8/0012; A61C 8/0022; A61C 8/0016; A61C 8/0018; A61C 8/0013
USPC ................................................. 433/172–176
See application file for complete search history.

(56) References Cited

U.S. PATENT DOCUMENTS

| 1,929,425 | A | 10/1933 | Hermann |
| 2,721,387 | A | 10/1955 | Ashuckian |

(Continued)

FOREIGN PATENT DOCUMENTS

| CA | 2506845 A1 | 7/2004 |
| CA | 2506854 A1 | 7/2004 |

(Continued)

OTHER PUBLICATIONS

More about stainless steel retreived from http://www.thomasnet.com/about/stainless-steel-80230204.html on Mar. 10, 2014.*

(Continued)

*Primary Examiner* — Heidi M Eide
(74) *Attorney, Agent, or Firm* — Schwegman Lundberg & Woessner, P.A.

(57) ABSTRACT

A dental implant can include a shaft defining a longitudinal axis and having an apical end, a coronal end, and an exterior surface. A portion of the exterior surface can include a porous material. The dental implant can include at least one thread, including a non-porous material, having an interior surface and a bone-engaging surface. The interior surface can engage and wind around the exterior surface of the shaft and the bone-engaging surface can extend outwardly from the exterior surface of the shaft. The shaft can include one or more channels configured to communicate a flowable material, stored within the shaft, to the exterior surface. Each channel can include an opening at the exterior surface to release the flowable material. At least one channel can extend between a cavity of the shaft and the exterior surface and can optionally be angled toward the apical end.

18 Claims, 4 Drawing Sheets

(56) References Cited

U.S. PATENT DOCUMENTS

| | | | |
|---|---|---|---|
| 3,314,420 | A | 4/1967 | Smith et al. |
| 3,423,830 | A | 1/1969 | Halpern et al. |
| 3,423,831 | A | 1/1969 | Semmelman |
| 3,435,526 | A * | 4/1969 | Brancato ............... 433/174 |
| 3,497,953 | A | 3/1970 | Weissman |
| 3,685,115 | A | 8/1972 | Scott |
| 3,713,860 | A | 1/1973 | Auskern |
| 3,740,851 | A | 6/1973 | Weissman |
| 3,797,113 | A | 3/1974 | Brainin |
| 3,849,887 | A | 11/1974 | Brainin |
| 3,896,547 | A | 7/1975 | Kulwiec |
| 3,905,109 | A | 9/1975 | Cohen et al. |
| 3,906,550 | A | 9/1975 | Rostoker et al. |
| 3,919,773 | A | 11/1975 | Freeman |
| 3,934,347 | A | 1/1976 | Lash et al. |
| 3,992,725 | A | 11/1976 | Homsy |
| 4,011,602 | A | 3/1977 | Rybicki et al. |
| 4,016,651 | A | 4/1977 | Kawahara et al. |
| 4,086,701 | A | 5/1978 | Kawahara et al. |
| 4,097,935 | A | 7/1978 | Jarcho |
| 4,122,605 | A | 10/1978 | Hirabayashi et al. |
| 4,131,597 | A | 12/1978 | Bluethgen et al. |
| 4,156,943 | A | 6/1979 | Collier |
| 4,178,686 | A | 12/1979 | Riess et al. |
| 4,195,366 | A | 4/1980 | Jarcho et al. |
| 4,199,864 | A | 4/1980 | Ashman |
| 4,229,170 | A | 10/1980 | Perez |
| 4,244,689 | A | 1/1981 | Ashman |
| 4,252,525 | A | 2/1981 | Child |
| 4,259,072 | A | 3/1981 | Hirabayashi et al. |
| 4,281,991 | A | 8/1981 | Michl et al. |
| 4,321,042 | A | 3/1982 | Scheicher |
| 4,375,967 | A | 3/1983 | Schaefer |
| 4,379,694 | A | 4/1983 | Riess |
| 4,381,918 | A | 5/1983 | Ehrnford |
| 4,411,624 | A | 10/1983 | Ogino et al. |
| 4,431,420 | A | 2/1984 | Adair |
| 4,439,152 | A | 3/1984 | Small |
| 4,448,758 | A | 5/1984 | Nagai et al. |
| 4,475,892 | A | 10/1984 | Faunce |
| 4,478,904 | A | 10/1984 | Ducheyne et al. |
| 4,483,678 | A | 11/1984 | Nishio et al. |
| 4,492,577 | A | 1/1985 | Farris et al. |
| 4,531,915 | A | 7/1985 | Tatum, Jr. |
| 4,531,916 | A | 7/1985 | Scantlebury et al. |
| 4,536,158 | A | 8/1985 | Bruins et al. |
| 4,548,959 | A | 10/1985 | Nagai et al. |
| 4,556,534 | A | 12/1985 | Burnett et al. |
| 4,708,652 | A | 11/1987 | Fujiu et al. |
| 4,713,006 | A | 12/1987 | Hakamatsuka et al. |
| 4,722,688 | A | 2/1988 | Lonca |
| 4,731,085 | A | 3/1988 | Koch |
| 4,737,411 | A | 4/1988 | Graves et al. |
| 4,738,062 | A * | 4/1988 | Dickey ............... 52/157 |
| 4,743,260 | A | 5/1988 | Burton |
| 4,744,757 | A | 5/1988 | Adair et al. |
| 4,744,759 | A | 5/1988 | Bowen |
| 4,820,157 | A | 4/1989 | Salvo |
| 4,842,517 | A | 6/1989 | Kawahara et al. |
| 4,871,384 | A | 10/1989 | Kasuga |
| 4,872,839 | A | 10/1989 | Branjnovic |
| 4,872,840 | A | 10/1989 | Bori |
| 4,877,400 | A | 10/1989 | Holsclaw |
| 4,880,610 | A | 11/1989 | Constantz |
| 4,906,190 | A | 3/1990 | Michna |
| 4,909,738 | A | 3/1990 | Ai et al. |
| 4,957,554 | A | 9/1990 | Mathers et al. |
| 4,957,819 | A | 9/1990 | Kawahara et al. |
| 4,960,733 | A | 10/1990 | Kasuga et al. |
| 4,969,817 | A | 11/1990 | Hiranuma et al. |
| 4,969,913 | A | 11/1990 | Ojima |
| 4,983,182 | A | 1/1991 | Kijima et al. |
| 5,000,685 | A | 3/1991 | Brajnovic |
| 5,002,488 | A | 3/1991 | Homsy |
| 5,004,421 | A | 4/1991 | Lazarof |
| 5,007,835 | A | 4/1991 | Valen |
| 5,009,709 | A | 4/1991 | Ibsen et al. |
| 5,049,074 | A | 9/1991 | Otani et al. |
| 5,055,497 | A | 10/1991 | Okada et al. |
| 5,061,285 | A | 10/1991 | Koch |
| 5,062,798 | A | 11/1991 | Tsuge et al. |
| 5,064,731 | A | 11/1991 | Miyazaki et al. |
| 5,076,789 | A | 12/1991 | Tanaka |
| 5,087,200 | A | 2/1992 | Brajnovic et al. |
| 5,120,340 | A | 6/1992 | Ducheyne et al. |
| 5,123,844 | A | 6/1992 | Wakai et al. |
| 5,125,839 | A | 6/1992 | Ingber et al. |
| 5,125,971 | A | 6/1992 | Nonami et al. |
| 5,139,424 | A | 8/1992 | Yli-Urpo |
| 5,152,687 | A | 10/1992 | Amino |
| 5,176,747 | A | 1/1993 | Panzera et al. |
| 5,180,303 | A | 1/1993 | Hornburg et al. |
| 5,186,626 | A | 2/1993 | Tanaka |
| 5,192,325 | A | 3/1993 | Kijima et al. |
| 5,194,000 | A | 3/1993 | Dury |
| 5,194,001 | A | 3/1993 | Salvo |
| 5,199,873 | A | 4/1993 | Schulte et al. |
| 5,205,745 | A | 4/1993 | Kamiya et al. |
| 5,232,365 | A | 8/1993 | Ikehara |
| 5,232,878 | A | 8/1993 | Kasuga et al. |
| 5,236,458 | A | 8/1993 | Ducheyne et al. |
| 5,238,405 | A | 8/1993 | Marlin |
| 5,254,005 | A | 10/1993 | Zuest |
| 5,282,861 | A | 2/1994 | Kaplan |
| 5,282,863 | A | 2/1994 | Burton |
| 5,288,232 | A | 2/1994 | Panzera et al. |
| 5,306,673 | A | 4/1994 | Hermansson et al. |
| 5,308,391 | A | 5/1994 | Komma et al. |
| 5,310,343 | A | 5/1994 | Hasegawa et al. |
| 5,312,254 | A | 5/1994 | Rosenlicht |
| 5,314,334 | A | 5/1994 | Panzera et al. |
| 5,342,201 | A | 8/1994 | Oden |
| 5,344,318 | A | 9/1994 | Wilson et al. |
| 5,344,457 | A | 9/1994 | Pilliar et al. |
| 5,346,397 | A | 9/1994 | Braiman |
| 5,415,546 | A | 5/1995 | Cox, Sr. |
| 5,419,702 | A | 5/1995 | Beaty et al. |
| 5,425,639 | A | 6/1995 | Anders |
| 5,425,640 | A | 6/1995 | Scharf |
| 5,439,380 | A | 8/1995 | Marlin |
| 5,443,515 | A | 8/1995 | Cohen et al. |
| 5,449,291 | A | 9/1995 | Lueschen et al. |
| 5,458,488 | A | 10/1995 | Chalifoux |
| 5,468,544 | A | 11/1995 | Marcolongo et al. |
| 5,470,230 | A | 11/1995 | Daftary et al. |
| 5,476,383 | A | 12/1995 | Beaty et al. |
| 5,549,123 | A | 8/1996 | Okuyama et al. |
| 5,554,665 | A | 9/1996 | Tateosian et al. |
| 5,562,733 | A | 10/1996 | Weissbach et al. |
| 5,571,016 | A | 11/1996 | Ingber et al. |
| 5,572,652 | A | 11/1996 | Robusto et al. |
| 5,575,652 | A | 11/1996 | Gaffar et al. |
| 5,584,688 | A * | 12/1996 | Sakuma et al. ............... 433/81 |
| 5,584,693 | A | 12/1996 | Nishihara |
| 5,591,030 | A | 1/1997 | Thiel et al. |
| 5,611,430 | A | 3/1997 | Albrecht et al. |
| 5,612,049 | A | 3/1997 | Li et al. |
| 5,614,330 | A | 3/1997 | Panzera et al. |
| 5,621,035 | A | 4/1997 | Lyles et al. |
| 5,624,262 | A | 4/1997 | Yarovesky et al. |
| 5,645,934 | A | 7/1997 | Marcolongo et al. |
| 5,674,069 | A | 10/1997 | Osorio |
| 5,676,745 | A | 10/1997 | Kelly et al. |
| 5,683,249 | A | 11/1997 | Ibsen et al. |
| 5,685,714 | A | 11/1997 | Beaty et al. |
| 5,695,337 | A | 12/1997 | Tyszblat Sadoun |
| 5,697,785 | A | 12/1997 | Delahaye |
| 5,697,976 | A | 12/1997 | Chesterfield et al. |
| 5,697,997 | A | 12/1997 | Aronsson et al. |
| 5,698,019 | A | 12/1997 | Frank et al. |
| 5,713,994 | A | 2/1998 | Kramer et al. |
| 5,723,007 | A | 3/1998 | Engel et al. |
| 5,727,943 | A | 3/1998 | Beaty et al. |
| 5,755,809 | A | 5/1998 | Cohen et al. |

(56) References Cited

U.S. PATENT DOCUMENTS

| | | |
|---|---|---|
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann, geb. Roth et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,947,893 A | 9/1999 | Agrawal et al. |
| 5,951,290 A | 9/1999 | Ardizio et al. |
| 5,951,293 A | 9/1999 | Billet et al. |
| 5,951,295 A | 9/1999 | Lyles et al. |
| 5,961,328 A | 10/1999 | Somborac et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,132,214 A | 10/2000 | Suhonen et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,213,775 B1 | 4/2001 | Reipur |
| 6,214,368 B1 | 4/2001 | Lee et al. |
| 6,224,662 B1 | 5/2001 | Nemeth |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,302 B1 | 1/2002 | Steidl et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,554,830 B1 * | 4/2003 | Chappius ............ 606/246 |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,559 B2 | 10/2004 | Golley |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,916,177 B2 | 7/2005 | Lin et al. |
| 6,918,766 B1 * | 7/2005 | Hall et al. ............ 433/201.1 |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 6,994,726 B2 | 2/2006 | Lin et al. |
| 7,011,522 B2 | 3/2006 | Panzera et al. |
| 7,291,012 B2 | 11/2007 | Lyren |
| 8,231,387 B2 | 7/2012 | Salvi et al. |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli, Jr. et al. |
| 2004/0024081 A1 | 2/2004 | Trieu et al. |
| 2004/0058299 A1 | 3/2004 | Molin et al. |

(56) References Cited

U.S. PATENT DOCUMENTS

| | | |
|---|---|---|
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0197737 A1 | 10/2004 | Uckelmann et al. |
| 2004/0234925 A1* | 11/2004 | Benhamou ............. 433/173 |
| 2004/0241614 A1 | 12/2004 | Goldberg et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0032025 A1* | 2/2005 | Bhaduri et al. ........... 433/201.1 |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0036253 A1* | 2/2006 | Leroux et al. ............. 606/73 |
| 2006/0075826 A1 | 4/2006 | Roberts et al. |
| 2007/0015110 A1 | 1/2007 | Zhang et al. |
| 2007/0020582 A1 | 1/2007 | Neumeyer |
| 2007/0111165 A1 | 5/2007 | Wallick et al. |
| 2007/0118221 A1 | 5/2007 | Robie et al. |
| 2007/0148621 A1 | 6/2007 | Yakir et al. |
| 2007/0184265 A1 | 8/2007 | Ranganathan et al. |
| 2007/0270858 A1* | 11/2007 | Trieu et al. ............. 606/73 |
| 2008/0033572 A1* | 2/2008 | D'Antonio et al. ........ 623/23.51 |
| 2008/0050699 A1 | 2/2008 | Zhang et al. |
| 2008/0241793 A1 | 10/2008 | Collins et al. |
| 2008/0261176 A1* | 10/2008 | Hurson ............. 433/174 |
| 2009/0036908 A1 | 2/2009 | Zokol et al. |
| 2009/0098510 A1 | 4/2009 | Zhang |
| 2009/0098511 A1 | 4/2009 | Zhang |
| 2012/0148983 A1* | 6/2012 | Mullen et al. ............. 433/174 |

FOREIGN PATENT DOCUMENTS

| | | |
|---|---|---|
| DE | 4209569 C2 | 11/1994 |
| DE | 19529036 A1 | 3/1997 |
| DE | 10105398 A1 | 8/2002 |
| EP | 0266313 A2 | 5/1988 |
| EP | 0271236 A1 | 6/1988 |
| EP | 0345581 A2 | 12/1989 |
| EP | 0366018 A1 | 5/1990 |
| EP | 0417018 A1 | 3/1991 |
| EP | 0467948 A1 | 1/1992 |
| EP | 0498923 A1 | 8/1992 |
| EP | 0333503 B1 | 2/1993 |
| EP | 0366018 B1 | 5/1993 |
| EP | 0560279 A1 | 9/1993 |
| EP | 0417018 B1 | 5/1994 |
| EP | 0498923 B1 | 5/1995 |
| EP | 0467948 B1 | 1/1996 |
| EP | 0806211 A1 | 11/1997 |
| EP | 0950421 A1 | 10/1999 |
| EP | 0560279 B1 | 6/2000 |
| EP | 0806211 B1 | 10/2002 |
| EP | 1281372 A1 | 2/2003 |
| EP | 1598028 A1 | 11/2005 |
| EP | 0950421 B1 | 10/2006 |
| EP | 1712205 A2 | 10/2006 |
| EP | 1598028 B1 | 12/2007 |
| FR | 2796265 A1 | 1/2001 |
| GB | 701802 A | 1/1954 |
| GB | 1526780 A | 9/1978 |
| GB | 2401867 B | 11/2004 |
| GB | 2416996 A1 | 2/2006 |
| JP | 61275205 A | 12/1986 |
| JP | 63290559 A | 11/1988 |
| JP | 1025849 A | 1/1989 |
| JP | 2002126071 A | 5/2002 |
| WO | WO-8604807 A1 | 8/1986 |
| WO | WO-8900410 A1 | 1/1989 |
| WO | WO-9011979 A1 | 10/1990 |
| WO | WO-9320773 A1 | 10/1993 |
| WO | WO-9421190 A1 | 9/1994 |
| WO | WO-9528973 A1 | 11/1995 |
| WO | WO-9721393 A1 | 6/1997 |
| WO | WO-9741809 A1 | 11/1997 |
| WO | WO-9830170 A1 | 7/1998 |
| WO | WO-0021455 A1 | 4/2000 |
| WO | WO-0132072 A2 | 5/2001 |
| WO | WO-0187193 A1 | 11/2001 |
| WO | WO-0234155 A1 | 5/2002 |
| WO | WO-0236039 A1 | 5/2002 |
| WO | WO-02062901 A1 | 8/2002 |
| WO | WO-02064100 A1 | 8/2002 |
| WO | WO-03065939 A1 | 8/2003 |
| WO | WO-03065996 A2 | 8/2003 |
| WO | WO-03078508 A1 | 9/2003 |
| WO | WO-03094774 A1 | 11/2003 |
| WO | WO-2004054464 A2 | 7/2004 |
| WO | WO-2006082610 A2 | 8/2006 |
| WO | WO-2007025290 | 3/2007 |
| WO | WO-2007027794 A1 | 3/2007 |
| WO | WO-2007086832 A2 | 8/2007 |
| WO | WO-2010002667 A1 | 1/2010 |

OTHER PUBLICATIONS integral. (n.d.). Dictionary.com Unabridged. Retrieved Mar. 21, 2015, from Dictionary.com website: http://dictionary.reference.com/browse/integral.*

"U.S. Appl. No. 12/167,107, Final Office Action mailed May 17, 2011", 13 pgs.

"U.S. Appl. No. 12/167,107, Non Final Office Action mailed Oct. 21, 2010", 14 pgs.

"U.S. Appl. No. 12/167,107, Notice of Allowance mailed Mar. 12, 2012", 11 pgs.

"U.S. Appl. No. 12/167,107, Response filed Mar. 18, 2011 to Non Final Office Action mailed Oct. 21, 2010", 11 pgs.

"U.S. Appl. No. 12/167,107, Response filed Aug. 17, 2011 to Final Office Action mailed May 17, 2011", 11 pgs.

"Flocculants, Binders, and Bonds", Chapter 11, Molecular Binders, (1995), 173-177.

"International Application Serial No. PCT/US2006/020130, International Search Report mailed Feb. 6, 2007", 7 pgs.

"International Application Serial No. PCT/US2006/033893, International Search Report dated Jan. 29, 2007" 1 pg.

"International Application Serial No. PCT/US2007/069562, International Search Report mailed Jul. 7, 2008", 1 pg.

"International Application Serial No. PCT/US2008/074616, International Search Report mailed Dec. 16, 2008", 4 pgs.

"International Application Serial No. PCT/US2008/074642, International Search Report mailed Feb. 12, 2009", 4 pgs.

"International Application Serial No. PCT/US2008/074645, International Search Report mailed Dec. 29, 2008", 9 pgs.

"International Application Serial No. PCT/US2008/074655, International Search Report mailed Feb. 18, 2009", 9 pgs.

"International Application Serial No. PCT/US2009/048456, International Search Report mailed Apr. 27, 2010", 5 pgs.

"International Application Serial No. PCT/US2009/048469, International Search Report mailed Oct. 19, 2009", 9 pgs.

"International Application Serial No. PCT/US2009/048476, International Search Report mailed Dec. 10, 2009", 13 pgs.

"International Application Serial No. PCT/US2009/048481, International Preliminary Report on Patentability mailed Jan. 5, 2011", 7 pgs.

(56) References Cited

OTHER PUBLICATIONS

"International Application Serial No. PCT/US2009/048481, International Search Report mailed Dec. 10, 2009", 2 pgs.

"International Application Serial No. PCT/US2009/048481, International Search Report mailed Dec. 10, 2009", (Dec. 10, 2009), 13 pgs.

"International Application Serial No. PCT/US2009/048481, Written Opinion mailed Dec. 10, 2009", 6 pgs.

"International Application Serial No. PCT/US2009/062308, International Search Report and Written Opinion mailed Jan. 21, 2010", 17 pgs.

"Peek-Classix", Information Sheet Invibio Ltd., Properties of Peek-Classix White Granular, (Nov. 2003).

"The Clinical Assessment of a Ceramic-Coated Transmucosal Dental Implant Collar", International Journal of Prosthodonics vol. 9, Issue 5, (1996), 466-472.

"Two Applications of Transmucosal Milled Ceramic in Implantology", Preliminary Clinical Examples; Implant Quintessence International vol. 27, Issue 8, (1996), 533-548.

Cass, Richard B, et al., "Innovative Ceramic-Fiber Technology Energizes Advanced Cerametrics", The American Ceramic Society, American Ceramic Society Bulletin, (Nov. 2003), 9701-9706.

Ganz, Scott D, "Presurgical Planning With CT-Derived Fabrication of Surgical Guides", J Oral Maxiofac Surg 63, Suppl 2, (2005), 59-73 pgs.

Kan, Joseph Y K, "Computer-Guided Immediate Provisionalization of Anterior Multiple Adjacent Implants: Surgical and Prosthodontic Rationale", Practical Procedures & Aethetic Dentistry, vol. 18, No. 10, (2006), 617-623 pgs.

Matinlinna, Jukka P, et al., "An Introduction to Silanes and Their Clinical Applications in Dentistry", The International Journal of Prosthodontics, vol. 17, No. 2, (2004), 155-164.

Reed, James S., "Chapter 24, Injection Molding", Principles of Ceramics Processing, 2nd Edition, New York : Wiley, (1995), 477-481.

Rosenfeld, Alan L, "Prosthetically Directed Implant Placement Using Computer Software to Ensure Precise Placement and Predictable Prosthetic Outcomes. Part 1: Diagnostics, Imaging, and Collaborative Accountability", International Journal of Periodontics & Restorative Dentistry, vol. 26, No. 3, (2006), 215-221 pgs.

Zhou, Yan, et al., "Shape Optimization of Randomly Oriented Short Fibers for Bone Cement Reinforcements", Materials Science & Engineering A 393, (2005), 374-381.

* cited by examiner

POROUS IMPLANT WITH NON-POROUS THREADS

CROSS-REFERENCE TO RELATED APPLICATIONS

This application is a continuation-in-part of, and claims priority to, U.S. patent application Ser. No. 12/167,107 filed Jul. 2, 2008, entitled "POROUS IMPLANT WITH NON-POROUS THREADS," the specification of which is herein incorporated by reference in its entirety.

BACKGROUND OF THE INVENTION

1. Field of the Invention

The present invention relates to bone implants and, in particular, to a threaded dental implant with improved osseointegration.

2. Description of the Related Art

Dental implants are commonly used as anchoring members for dental restorations to provide prosthetic teeth at one or more edentulous sites in a patient's dentition at which the patient's original teeth have been lost or damaged. Typically, implant systems can include a dental implant made from a suitable biocompatible material, such as titanium. The dental implant can be threaded into a bore, which is drilled into the patient's mandible or maxilla at the edentulous site. The implant provides an anchoring member for a dental abutment, which, in turn, provides an interface between the implant and a dental restoration. The restoration can be a porcelain crown fashioned according to known methods.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In this final stage, the temporary prosthesis or healing member is removed and replaced with the permanent prosthesis, which is attached to the abutment with cement or with a fastener, for example. Alternative single stage implants with integral emergence profiles or one-piece implants with integral abutments may be used that extend through the transgingival layer so that the gingiva need not be reopened to access the implant.

Patients prefer to leave after initial surgery with some type of restoration and studies indicate that healing of both soft and hard tissue may be improved if the implant is loaded after surgery. Post-surgical loading, even if less than a full load of occlusion, however, is sufficient to displace the implant. Thus, threads may be used to secure the implant directly to the bone to achieve initial stability.

SUMMARY

The present inventors have recognized, among other things, that a dental implant can become displaced due to improper in-growth of dental bone into the dental implant. In such instances, the dental implant can become displaced during tensile and compressive forces or bending and twisting forces generated during a chewing motion.

One way to improve osseointegration onto an implant, and in turn improve the long term stability of the implant, is to provide a porous material on the implant that the bone can grow into. Such a porous material can also increase short term stability for immediate loading due to a large friction coefficient with surrounding bone.

Providing a porous material only on the surface of the implant, however, can result in bone growth only near the surface of the implant. The final stability of the implant can be increased if bone growth extends deeper than just near the surface of the implant. Such a porous structure, however, may not provide sufficient strength to use as threads on a screw-type implant to resist mastication forces. The present inventors have thus conceived a porous implant configuration that provides sufficient initial and long-term stability when embedded in biological tissue, such as bone.

To better illustrate the porous implants with non-porous threads and related methods disclosed herein, a non-limiting list of examples is provided here:

In Example 1, a dental implant comprises a shaft defining a longitudinal axis and having an apical end, a coronal end, and an exterior surface, a portion of the exterior surface including a porous material; and at least one thread, including a non-porous material, having an interior surface and a bone-engaging surface, the interior surface engaging and winding around the exterior surface of the shaft, the bone-engaging surface extending outwardly from the exterior surface of the shaft.

In Example 2, the dental implant of Example 1 optionally further comprises a non-porous head portion, including a male or female interface for coupling to an abutment, positioned at the coronal end of the shaft.

In Example 3, the dental implant of Example 2 is optionally configured such that the coronal end of the shaft includes a coronally accessible cavity configured for receiving and coupling to the head portion.

In Example 4, the dental implant of any one or any combination of Examples 2 and 3 is optionally configured such that the at least one thread is integrally formed with the head portion.

In Example 5, the dental implant of any one or any combination of Examples 2-4 is optionally configured such that the at least one thread includes a plurality of helical parallel threads, each thread winding apically away from the head portion and concentric about the longitudinal axis.

In Example 6, the dental implant of any one or any combination of Examples 1-5 is optionally configured such that the interior surface of the at least one thread defines a central opening configured to receive and engage at least the coronal end of the shaft.

In Example 7, the dental implant of any one or any combination of Examples 1-6 is optionally configured such that the exterior surface includes a groove for receiving a portion of the at least one thread.

In Example 8, the dental implant of any one or any combination of Examples 1-7 is optionally configured such that the shaft includes one or more channels configured to communicate a flowable material, stored within the shaft, to the exterior surface, each channel including an opening at the exterior surface.

In Example 9, the dental implant of Example 8 is optionally configured such that each opening, at the exterior surface, is positioned between successive windings of the at least one thread.

In Example 10, the dental implant of any one or any combination of Examples 8 and 9 is optionally configured such that at least one channel, of the one or more channels, extends between a cavity of the shaft and the exterior surface.

In Example 11, the dental implant of Example 10 is optionally configured such that the at least one channel is oriented at an angle toward the apical end, relative to a plane that is orthogonal to the longitudinal axis, from the cavity to the exterior surface.

In Example 12, the dental implant of any one or any combination of Examples 10 and 11 is optionally configured such that the flowable material is pre-loaded and stored in the cavity.

In Example 13, the dental implant of any one or any combination of Examples 8 and 9 is optionally configured such that the flowable material is pre-loaded and stored in at least one channel, of the one or more channels.

In Example 14, the dental implant of any one or any combination of Examples 8-13 is optionally configured such that the flowable material includes at least one of a resorbable polymer, a hydrophilic material, an in-growth promotion material, an insertion aiding material, or an antibiotic.

In Example 15, the dental implant of any one or any combination of Examples 8-14 is optionally configured such that the flowable material includes a powder configured to be hydrated and form a solution.

In Example 16, the dental implant of any one or any combination of Examples 1-15 is optionally configured such that the bone-engaging surface is coated with a material deposited by a chemical vapor deposition process.

In Example 17, the dental implant of any one or any combination of Examples 1-16 is optionally configured such that the porous material includes at least one of an organic bone graft, a resorbable polymer, a non-resorbable polymer, a synthetic bone material, tantalum, or collagen.

In Example 18, a method comprises inserting a dental implant, including a shaft having a cavity, an exterior surface, and one or more channels including an opening at the exterior surface, and at least one thread, formed of a material different than the shaft and configured to engage and wind around the exterior surface, into a dental bone cavity; and permitting at least a portion of a flowable material to flow through the one or more channels, and into the dental bone cavity, including delivering at least one of a resorbable polymer, a hydrophilic material, an in-growth promotion material, an insertion aiding material, or an antibiotic to the dental body cavity.

In Example 19, the method of Example 18 is optionally configured such that inserting the dental implant includes inserting a pre-loaded amount of the flowable material stored within the cavity.

In Example 20, the method of Example 19 is optionally configured such that permitting the flowable material to flow through the one or channels includes permitting the flowable material to utilize gravity and flow through a channel oriented at a downward angle, relative to a plane that is orthogonal to a longitudinal axis of the dental implant, between the shaft and the exterior surface.

In Example 21, the method of any one or any combination of Examples 18-20 is optionally configured such that inserting the dental implant includes inserting a porous exterior surface portion, of the shaft, and a non-porous bone-engaging surface, of the at least one thread.

In Example 22, the method of any one or any combination of Examples 18-21 optionally further comprises hydrating the flowable material, including a powder, after inserting the dental implant into the dental bone cavity.

In example 23, the method of any one or any combination of Examples 18-22 optionally further comprises permitting the flowable material to form a membrane between at least a portion of the exterior surface and a portion of the dental bone cavity.

These and other examples, advantages, and features of the present porous implants with non-porous threads and related methods will be set forth in part in the following Detailed Description and the accompanying drawings. This Overview is intended to provide non-limiting examples of the present subject matter—it is not intended to provide an exclusive or exhaustive explanation. The Detailed Description and drawings are included to provide further information about the present porous implants with non-porous threads and related methods.

DETAILED DESCRIPTION

Figures 1, 2:
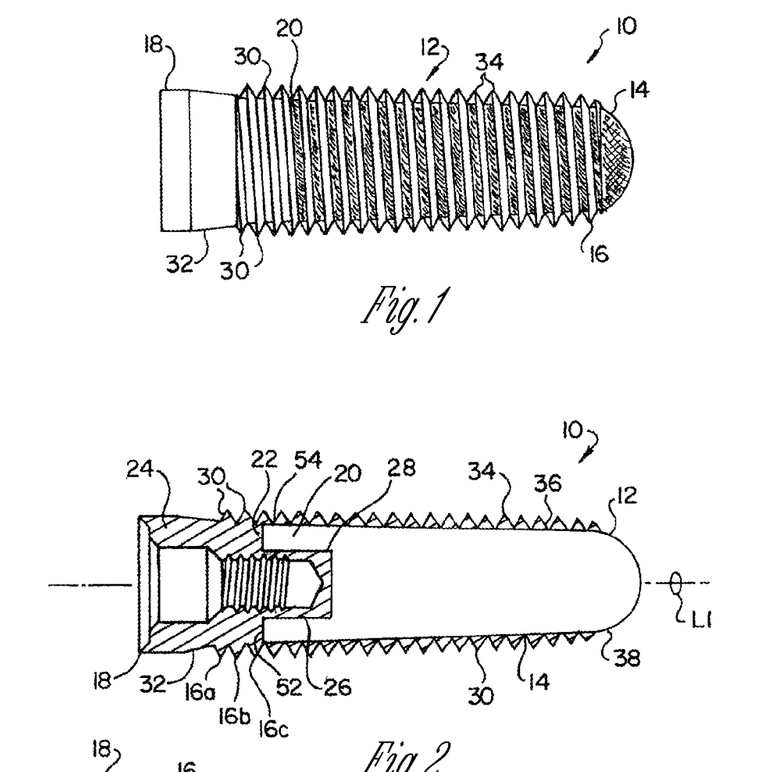
FIG. 1 is an elevational view of a dental implant in accordance with at least one example of the present invention.
FIG. 2 is a cross-sectional view of the dental implant of FIG. 1 in accordance with at least one example of the present invention.
Figure 3:
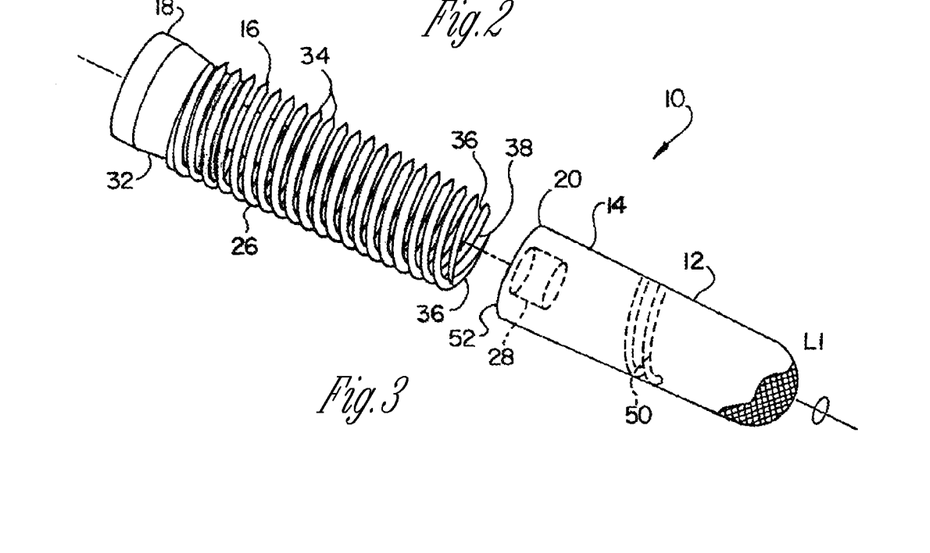
FIG. 3 is an exploded view of the dental implant of FIG. 1 in accordance with at least one example of the present invention.

Referring to FIGS. 1-3, an implant 10 can be used to anchor prosthetic devices to bone. In one form, the implant 10 can be a dental implant for anchoring an abutment or other dental prosthesis to a jaw bone. The implant 10 generally defines a longitudinal axis L1 (shown in FIG. 2) and includes a shaft 12 made of a porous material for improving osseointegration onto the implant 10 as explained in greater detail below. The shaft 12 can include an exterior surface 14 and at least one non-porous thread 16 winding around, and engaging, the exterior surface 14, and extending outwardly from the exterior surface 14 for engaging bone. While the illustrated shaft 12 is substantially porous, shaft 12 can have a non-porous, axially extending core. Such a core could be made of titanium, ceramic or other non-porous material.

The implant 10 can include a non-porous head portion 18 located at a coronal end portion 20 of the shaft 12. The non-porous head portion 18 can be made of a suitable biocompatible material, such as titanium, although the head portion may also be made of other biocompatible materials such as at least one of the following: titanium alloy, stainless steel, zirconium, cobalt-chromium molybdenum alloy, ceramic, a polymer, and a composite material.

Referring to FIG. 2, the head portion 18 can form an axial bore 22 for receiving the bottom of an abutment and/or an abutment connector extending out of the abutment to secure the abutment to the implant 10. For example, the bore 22 can be internally threaded to receive the abutment connector, and can have an anti-rotational flat or surface 24 (such as a hexagon, for example) to receive a corresponding interface from the abutment.

The head portion 18 can have an apical extension 26 to contain the bore 22 entirely in the stronger, solid material of the head portion 18 rather than the porous material at the shaft 12. The exposure of the exterior porous material can be increased by placing the extension 26 in a coronally accessible cavity 28 formed at the coronal end portion 20 of the shaft 12. Alternatively to the bore 22, the head portion 18 can provide a male interface for a separate female abutment. The extension, although not needed to form a bore, can be used, to provide extra surface area for the shaft 12 to be press-fit against the head portion 18. In another example, the implant 10 can be a one-piece implant where the head portion 18 also includes an integral abutment or the implant 10 can be a single-stage dental implant with an integral transmucosal portion.

In the illustrated form, the helical thread 16 includes three helical parallel threads 16a, 16b, and 16c although more or less may be provided. One or more coils 30 of the threads 16a, 16b, and 16c can be formed integrally with a main body 32 forming the head portion 18. The threads 16a, 16b, and 16c can extend and wind apically away from the main body 32, concentric about longitudinal axis L1, and form uniformly spaced coils or rotations 34 as it extends axially along the shaft 12.

The non-porous thread 16 can include a helical, interior surface 36 that faces the shaft 12 so as to define a central opening 38 configured for receiving the shaft 12 by at least a press-fit. The exterior surface 14 of the shaft 12 can, due to the porous material, have a sufficient coefficient of friction with the interior surface 36 to restrict axial motion of the shaft 12 relative to the thread 16. Additionally, the exterior surface 14 of the shaft can define a helical groove 50 (shown in dashed line) for receiving the helical thread 16 to further restrict motion between the shaft 12 and the thread 16.

The head portion 18 and the non-porous thread 16 can secure the shaft 12 without other devices. It will be appreciated, however, that the shaft 12 can additionally be attached to the head portion 18 using other mechanisms, such as adhesive, welding, diffusion bonding, sintering, fasteners and so forth.

The coronal end portion 20 of the shaft 12 is annular and can extend between the apical extension 26 of the head portion 18 and the threads 16 for a tight press-fit between the two structures. In one form, this configuration will maintain an annular coronal face 52 of the coronal end portion 20 abutted against an annular, apically-facing shoulder 54 (FIG. 2) formed by the head portion 18 and facing the central opening 38.

The thread 16 can be integrally formed with the head portion 18, or attached to the head portion 18 by other bonding processes. The thread 16 can be made of the same material as the head portion 18, as described above. In one form, the thread 16 can be made of titanium. The head portion 18 can be manufactured by using a screw-machine, or similar device, to machine the head portion. Wire electrical discharge machining (EDM) can used to cut the thread 16 without imparting any cutting loads to the thread 16, thereby maintaining the shape of the helical thread.

In the configuration described, the exterior surface 14 of the shaft 12 can be exposed as a spiraling surface between coils 34 of the thread 16 to receive osseointegrating bone. Osseointegration occurs and bone growth can extend deeper on the shaft 12 than the surface 14 of the shaft 12, such that the bone can be free to grow anywhere within the shaft when the shaft 12 is substantially porous.

As described herein, the shaft 12 can be made of a porous material. Examples of porous material can include a material produced using Trabecular Metal™ technology generally available from Zimmer, Inc., of Warsaw, Ind. Trabecular Metal™ is a trademark of Zimmer Technology, Inc. Such a material can be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. Other metals such as niobium, or alloys of tantalum and niobium with one another or with other metals can also be used.

Figure 4:
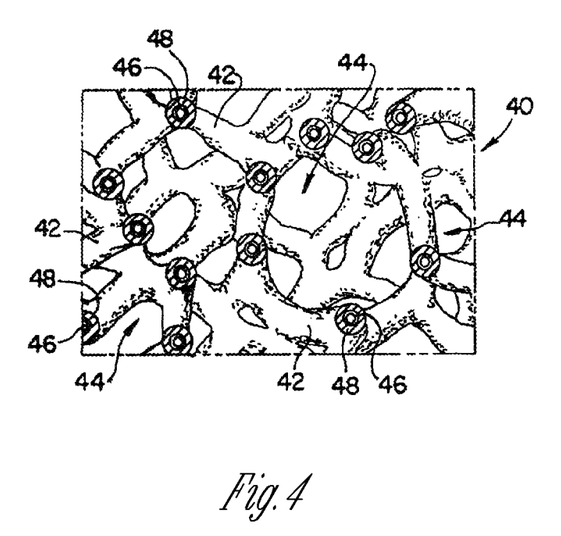
FIG. 4 is an enlarged fragmentary view of the portion of the porous tantalum forming the dental implant of FIG. 1 in accordance with at least one example of the present invention.

Generally, as shown in FIG. 4, the porous tantalum structure 40 can include a large plurality of ligaments 42 defining open spaces 44 therebetween, with each ligament 42 generally including a carbon core 46 covered by a thin film of metal 48 such as tantalum, for example. The open spaces 44 between the ligaments 42 can form a matrix of continuous channels having no dead ends, such that growth of cancellous bone through porous tantalum structure 40 is uninhibited. The porous tantalum can include up to 75%-85% or more void space therein. Thus, porous tantalum can be a lightweight, strong porous structure which is substantially uniform and consistent in composition, and closely resembles the structure of natural cancellous bone, thereby providing a matrix into which cancellous bone may grow to anchor implant 10 into the surrounding bone of a patient's jaw, which increases the stability of the implantation. The rough exterior surface of such porous metal shaft can provide a relatively high friction coefficient with adjacent bone forming the bore that receives the implant to further increase initial stability in addition to that provided by the thread 16. This structure can produce superior esthetic results by restricting movement of the implant.

The porous tantalum structure 40 can be made in a variety of densities in order to selectively tailor the structure for particular applications. In particular, as discussed in the above-incorporated U.S. Pat. No. 5,282,861, the porous tantalum can be fabricated to virtually any desired porosity and pore size, and can thus be matched with the surrounding natural bone in order to provide an improved matrix for bone ingrowth and mineralization. Such as, a gradation of pore size on a single implant such that pores are larger on an apical end to match cancellous bone and smaller on a coronal end to match cortical bone, or even to receive soft tissue ingrowth. Also, the porous tantalum can be made denser with fewer pores in areas of high mechanical stress. Instead of smaller pores in the tantalum, the porous tantalum can be made denser by filling all or some of the pores with a solid material which is described in further detail below.

To provide additional initial mechanical strength and stability to the porous structure, the porous structure can be infiltrated with a filler material such as a non-resorbable polymer or a resorbable polymer. Examples of non-resorbable polymers for infiltration of the porous structure can include a polyaryl ether ketone (P AEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers can include polylactic co-glycolic acid (PLGA), polylactic acid (PLA), polyglycolic acid (PGA), polyhydroxybutyrate (PHB), and polyhydroxyvalerate (PHV), and copolymers thereof, polycaprolactone, polyanhydrides, and polyorthoesters. By providing additional initial mechanical strength and stability with a resorbable filler material, a titanium reinforcing implant core can potentially be removed from the implant. For example, the resorbable material can resorb as the bone grows in and replaces it, which maintains the strength and stability of the implant.

With this porous structure, in one form, the implant 10 can be approximately 3.7 mm or greater in order to sustain intraoral mechanical forces. The implant 10 can have a generally cylindrical outer surface or can taper so that its diameter increases as it extends coronally to further increase friction with bone within a bore in the patient's jaw receiving the implant.

In use, the implant 10 can be screwed into a bore drilled into a patient's jaw bone at an edentulous site to provide a firm initial seating of the implant 10 into the bore. Thereafter, the bone tissue surrounding the implant 10 can osseointegrate into the open spaces 44 of the porous metal shaft 12, thereby firmly anchoring the shaft 12 and the implant 10 into the surrounding bone structure. This osseointegration can also provide a favorable environment for load transfer to the bone since the porous material has a stiffness similar to that of cancellous bone. Consequently, this can stimulate more complete and stronger bone growth around the implant.

While implant 10 can be used as a dental implant, it will be understood that the structure of an implant with a porous metal or porous tantalum portion press fit into helical threads may be used anywhere on an animal or human body.

Instead of, or in addition to, porous tantalum or porous metal, a shaft can be made of a first material that promotes bone growth or strengthens the implant instead of porous tantalum, such as organic bone graft (e.g., autograft, allograft, xenograft), resorbable polymer (e.g., polylactic co-glycolic acid (PLGA), polylactic acid (PLA), polyglycolic acid (PGA), polyhydroxybutyrate (PHB), and polyhydroxyvalerate (PHV)), non-resorbable polymer, synthetic bone material such as hydroxyapatite (HA), or collagen. A shaft of such material can be initially formed and then press-fit into a thread of a different material, as described above, or the thread may be formed on the shaft in other ways.

Figure 5A:
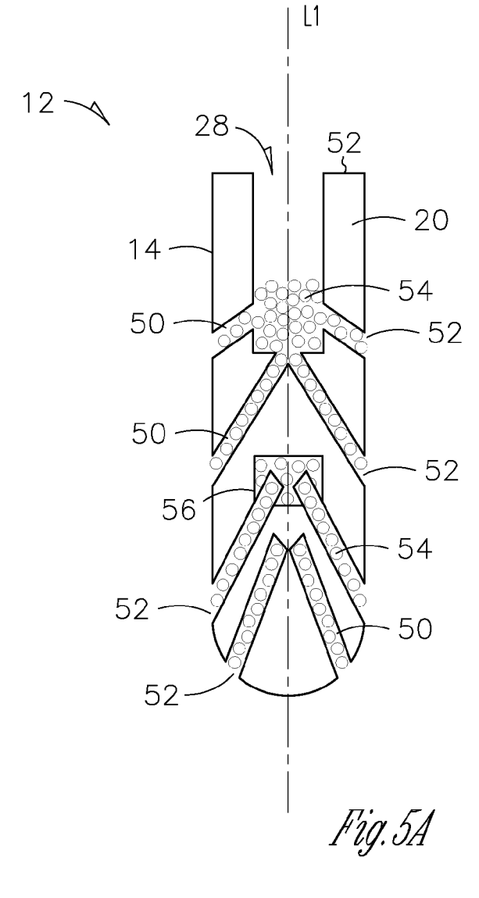
FIGS. 5A-5B are cross-sectional views of dental implants in accordance with at least two examples of the present invention.
Figure 5B:
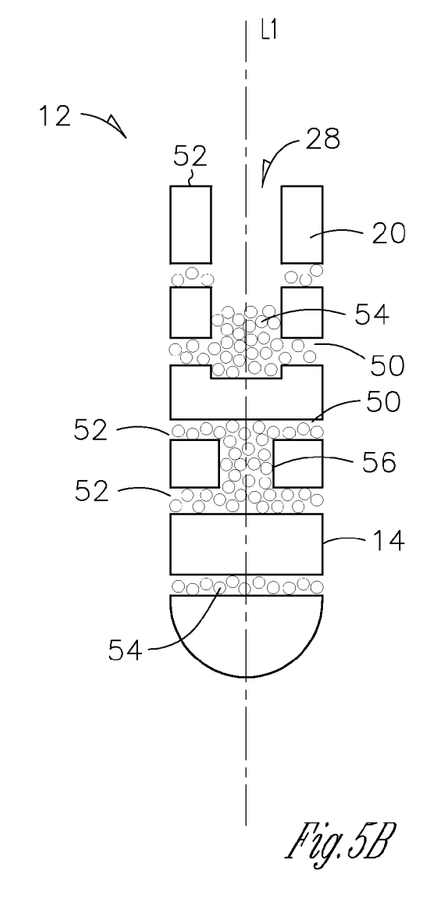

As illustrated in FIGS. 5A and 5B, the shaft 12 can further include one or more channels 50 including openings 52 at the exterior surface 14. The one or more channels 50 can be configured to communicate a flowable material 54, stored within the shaft 12, to the exterior surface 14. In an example, the one or more channels 50 can extend from the accessible cavity 28 of the shaft 12 to the exterior surface 14. The accessible cavity 28 can be in fluid communication with the exterior surface 14 by way of the one or more channels 50. Alternatively or additionally, the one or more channels 50 can extend from an interior of the shaft 12 or a receptacle 56, distinct from the accessible cavity 28, to the exterior surface 14. The openings 52 at the exterior surface 14 can be sized and shaped to allow the flowable material 54 to flow from the accessible cavity 28, receptacle 56, or other interior portion of the shaft to the surrounding dental cavity. Once in the dental cavity, the flowable material 54 can form a membrane between a portion of the exterior surface of the dental implant 14 and the dental cavity or bone.

In some examples, at least one channel 50 can be oriented at an angle toward the apical end, relative to a plane or axis that is orthogonal to the longitudinal axis L1, as illustrated in FIG. 5A. In such examples, the implant 10 can be oriented in a lower jaw bone such that the one or more channels 54 can utilize gravity to allow the flowable material 54 to flow through a channel 50 oriented at a downward angle from the accessible cavity 28. In one or more example at least one the channels 50 can be oriented such that injection pressure can direct the flowable material towards the apical end of the implant 10. Alternatively or additionally, one or more channels 50 can be directed towards the middle or coronal area of the implant 10 such that the flowable material is dispersed into the middle or coronal area.

A syringe or other instrument can be used to provide injection pressure for delivery of the flowable material. In some examples, insertion of an abutment screw in implant 10 can displace the flowable material 54 such that the flowable material flows through channels 50 to the exterior surface 14 of the implant 10. In such examples, the flowable material 54 can include a putty-like substance configured such that an increase in shear stress or tensile stress causes the flowable material to flow within the channels 50.

The orientation of a channel or channels can be configured to deliver the flowable material 54 to a predetermined location within the implant 10, on the exterior surface 14, or within the dental cavity. For example, bone loss due to bacterial infection can typically occur at the coronal aspect of the implant 10. In such instances, the flowable material 54, including antimicrobial agents, can be directed to the infectious area. A high concentration of growth factors can adversely effect implantation or fixation of the implant 10. In an example, the flowable material 54 can include a time release growth factor to mitigate the adverse effects.

As shown in FIGS. 5A and 5B, the shaft 12 can include one or more receptacle 56 configured such that the flowable material 54 can be directed to the one or more channels 50. The receptacle 56 can include flowable material 54 formulated for a location of the one or more channel 50 connected to the receptacle. For example, a receptacle 56 connected to a channel 50 directed toward an apical end can include flowable material with a bone in-growth promoter to aid fixation. Additionally or alternatively, the receptacle 56 connected to a channel 50 that is directed toward a coronal end can include flowable material with an antimicrobial agent to aid in infections.

In some examples, at least one channel 50 can be parallel to at least one other channel 50. In some examples, at least one channel 50 is not parallel to at least one other channel 50. In some examples, as illustrated in FIG. 5B, at least one channel 50 can be oriented orthogonal to a longitudinal axis L1 of the dental implant.

The channels 50 can include a variety of shapes and sizes. For example, the channels 50 can be formed as circles, ovals, triangles, squares, rectangles, hexagons, heptagons, octagons, or combinations thereof. The channels 50 can have a uniform diameter. In some examples, the diameter can vary. In some examples, each of the one or more channels 50 can have the same diameter. In some examples, the one or more channels 50 can have different diameters with respect to each other. In some examples, the width or diameter of the channels 50 can range from about 0.25 millimeters (mm) to about 3.0 mm.

In an example, the channels 50 can include a non-porous interior surface. For example, one or more channels 50 can include an insertable non-porous sleeve such that flow of the flowable material 54 is facilitated. In an example, one or more channels 50 can be bored or drilled into the shaft 12. Alternatively or additionally, one or more channels 50 can include an interior surface including the same porous material included in the shaft 12.

The number and location of the channels 50 can also vary. A factor in determining the number and location of the channels 50 can depend on the quality of the patient's dental bone.

For example, if dental bone positioned coronal to the prosthetic tooth is more damaged than dental bone positioned apically from the prosthetic tooth, it can be desirable to provide additional stabilization along the portion of the dental bone that is more damaged. In that instance, a dental implant with one or more channels positioned towards the coronal end of the shaft 12 can be used. As a result, when flowable material 54 is introduced into the cavity and allowed to flow through the channels 50 into the dental cavity through the openings 52, the flowable material can be introduced and form a stabilizing layer between the dental implant 12 and the dental bone that is more damaged.

In an example, the flowable material 54 can be pre-loaded and stored within the accessible cavity 28. In another example, the flowable material 54 can be pre-loaded and stored in at least one channel, of the one or more channels 50. The flowable material can be pre-loaded in the dental implant 10 by a physician at or about the time of a procedure or can be pre-loaded by a manufacturer and packaged.

In some examples, the flowable material 54 can be at least one of a resorbable polymer, a hydrophilic material, an ingrowth material, or an antibiotic. For example, the flowable material 54 can include a blend of a resorbable polymer and at least one of an allograft material, an autograft material, and a xenograft material. The term "resorbable" is used herein to refer to a material that maintains its structural integrity during an initial period of time, but is capable of being disintegrated and absorbed by a living body over time. For example, resorbable polymers suitable for use with the present dental implants 10 can include, but are not limited to, polylactic acid, polyglycolic acid, polyhydroxybutyrate, and polyhydroxyvalerate, and copolymers thereof, polycaprolactone, polyanhydrides, polyorthoesters, and other biodegradable polymers. Moreover, allograft materials suitable for use with the present dental implants 10 can include, but are not limited to, demineralized bone matrix (DBM), such as DBM sold by Zimmer Dental under the trade name Puros®, bone morphogenetic protein (BMP), human growth hormone (HGH), other regenerative materials derived from human body, or mixtures and blends thereof.

The flowable material can include at least one of an allograft material, an autograft material, and a xenograft material, combined with saline or blood to form a slurry capable of flowing through the channels 50. Such an example can benefit an extraction area where it is desirable to have a material packed in the site such that it fills the space between the implant and the extraction area.

The flowable material 54 can include a material capable of hardening to form a membrane between at least a portion of the implant 10 and the dental cavity. For example, one or more channel 50 near the coronal end of the implant can configured to provide a flowable material with a hardening agent. In an example, grafting material can be used to fill-in defects or gaps between the implant and dental cavity toward the coronal end of the dental cavity. Grafting material delivered, if left uncovered, can disperse before healing occurs. To prevent this, the implant 10 can be configured to deliver a liquid membrane injected and ported out the coronal aspect via one or more channel 50 of the implant. The flowable material 54 can flow from the implant 10 and over the graft such that the membrane that forms from the hardened flowable material covers the grafting material. The membrane can harden and seal to the implant 10 and the peripheries of the graft. The membrane can be resorbable or removed after healing has occurred.

The flowable material 54 can include other ingredients. In an example, the flowable material 54 can include an anti-inflammatory medication to expedite healing of the surgically created dental cavity or an antibiotic medication to prevent infections of the surgically created dental cavity. In an example, the flowable material can include a radio-opaque substance, such as barium sulphate, so that the flowable material can be readily locatable by X-ray or other imaging means. Such examples can aid a physician in determining fixation of the dental implant 10.

In examples, the flowable material can include a time release agent, which can be dispersed using the natural flow of body fluids or induced such that the flowable material flows within the implant 10. Additionally or alternatively, the flowable material can include charged or magnetized particles, such that natural or induced electromagnetic forces can be used to direct the flowable material 54 toward the exterior surface 14. In an example, a current can be applied directly or remotely through induction phenomena to the implant 10 such that the flowable material can be displaced and flow through the channels 50. In such an example, the implant 10 can be formed from of a nickel-titanium memory alloy or similar material.

The flowable material 54 can be delivered to the dental bone cavity in a semi-solid, liquid, or powder state to facilitate fixation or stabilization between the dental bone and the dental implant 10. Upon insertion, the flowable material 54 can be hydrated so as to form a material capable of flowing within, for example, one or more channels 50. The flowable material 54 can be hydrated with the assistance of a physician, by applying a fluid directly to the dental implant 10, or by the natural oral fluids of a patient. For example, the exterior surface 14 of the implant shaft 12 can include a hydrophilic material configured to promote hydration of the flowable material 54. Upon curing, the flowable material 54 can provide initial stability to the dental implant 10 and dental bone interface, and can act to resist tensile and compressive forces or bending and twisting generated by the chewing motion of jaw bones. In an example, the exterior surface 14 can include a hydrophilic material.

In addition to providing stability to the dental implant 10, the flowable material 54 can also act as a medium for ingrowth of dental bone around and into the dental implant 10. For example, the cured flowable material 54 can include a stiffness less than the dental implant 10, but greater than that of the dental bone. In such an example, the cured flowable material 54 can provide a buffer that can lead to improved osseointegration and increased dental bone growth around the dental implant 10, as compared to an inserted dental implant 10 without the flowable material 54.

Figure 6:
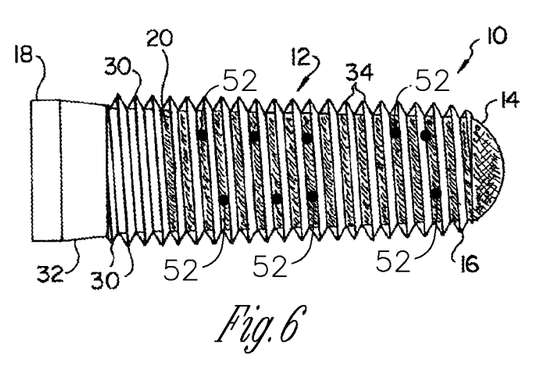
FIG. 6 is an elevational view of a dental implant in accordance with at least one example of the present invention.

As illustrated in FIG. 6, the openings 52 can be positioned between successive windings or coils 34 of the at least one thread 16. In an example, the one or more openings 52 include a diameter smaller than a distance between the successive windings 34. Such a configuration can permit the flowable material to flow unimpeded from the interior of the shaft 12 to the surrounding dental cavity. In an example, the openings 52 can be placed at one or more successive windings or coils 34. Such example can provide a benefit of bone-ingrowth of the one or more successive windings or coils 34.

In an example, the bone engaging-surface of the at least on thread 16 can be coated with a material deposited by a chemical vapor deposition (CVD) process. A CVD process can include a infiltrating or coating a carbon skeleton of the at least one thread 16 with a first layer of biocompatible metal, such as tantalum, to produce a low density material, and then plated with a second layer of tantalum to produce a high density material. As discussed in the above-incorporated U.S. Pat. No. 5,282,861, the material can be deposited on the bone engaging surface by a CVD process. In an example, the material deposited on the bone engaging surface is tantalum. One or more other materials, e.g., in addition to tantalum, including alloys thereof, can be used, such as, for example, niobium. The deposited material can lead to improved osseointegration or increased dental bone growth around the dental implant 10.

A method can include inserting a dental implant, including a shaft having a cavity, an exterior surface, and one or more channels including an opening at the exterior surface, and at least one thread, formed of a material different than the shaft and configured to engage and wind around the exterior surface, into a dental bone cavity. The method can include permitting at least a portion of a flowable material to flow through the one or more channels, and into the dental bone cavity, including delivering at least one of a resorbable polymer, a hydrophilic material, an in-growth promotion material, or an antibiotic to the dental body cavity.

In an example, inserting the dental implant can include inserting a pre-loaded amount of the flowable material stored within the cavity. The pre-loaded amount of flowable material can include a pre-measured amount or an amount of flowable material measured by a physician. The amount can depend upon the composition of the flowable material, the jaw bone condition of the patient, medical prognoses of the patient, or the size of the dental implant, among other factors.

In an example, inserting the dental implant can include inserting a porous exterior surface portion, of the shaft, and a non-porous bone-engaging surface, of the at least one thread. As described herein, the at least one thread can receive, through an open end, the shaft of the dental implant.

In an example, permitting the portion of flowable material to flow through the one or more channels can include permitting the portion of flowable material to utilize gravity and flow through a channel oriented at a downward angle, relative to a plane that is orthogonal to a longitudinal axis of the dental implant, between the shaft and the exterior surface. In such an example, the channels can be positioned as described in reference to FIG. 5A.

The method can include hydrating the flowable material after inserting the dental implant into the dental bone cavity. In an example, the flowable material is hydrated by a physician. The flowable material can be hydrated with any suitable fluid. In an example, the flowable material is hydrated by a patient's oral fluid. As described herein, the dental implant can include a hydrophilic material to aid in hydration of the flowable fluid.

In an example, the flowable material can be added during implantation to assist in the placement of the dental implant 10 through lubrication, cooling, or softening of the implantation site. Such a process can be reversed after implantation to help secure the implant 10 within the dental cavity. For example an acid, such as acetic acid, can be injected into the implant or along the thread to initially soften the bone so that implant can be more easily inserted. A pilot drill can be used to create a small hole within the dental bone for the acid to be placed. The acid can remove calcium from the bone leaving behind a collagen matrix, sufficiently pliable for the thread to expand the site for the implant 10 to be inserted. After placement, a flowable material 54 including calcium or buffers to neutralize the acid can be injected into the implant or around the implant. The flowable material can then flow to the implantation site and replenish the calcium in the bone. Such examples can restore the bone to approximately its initial strength, helping lock the implant 10 into the dental cavity site.

Each of these non-limiting examples can stand on its own, or can be combined in any permutation or combination with any one or more of the other examples.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other embodiments can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:
1. A dental implant, comprising:
a shaft defining a longitudinal axis and having an apical end, a coronal end, and an exterior surface, a portion of the exterior surface including a porous material;

a non-porous head portion, including a male or female interface for coupling to an abutment, the head portion attached to the coronal end of the shaft; and at least one thread integrally formed with the head portion and the at least one thread and the head portion comprising a separate element from the shaft prior to attachment of the head portion with the shaft, the at least one thread including a non-porous material and having an interior surface and a bone-engaging surface, the interior surface configured to engage and wind around the exterior surface of the shaft to form a porous-non-porous material interface between the interior surface and the exterior surface of the shaft, the bone-engaging surface extending outwardly from the exterior surface of the shaft, wherein the exterior surface of the shaft is exposed.

2. The dental implant of claim 1, wherein the coronal end of the shaft includes a coronally accessible cavity configured for receiving and coupling to the head portion.

3. The dental implant of claim 1, wherein the at least one thread includes a plurality of helical parallel threads, each thread winding apically away from the head portion and concentric about the longitudinal axis.

4. The dental implant of claim 1, wherein the interior surface of the at least one thread defines a central opening configured to receive and engage at least the coronal end of the shaft.

5. The dental implant of claim 1, wherein the exterior surface includes a groove for receiving a portion of the at least one thread.

6. The dental implant of claim 1, wherein the shaft includes one or more channels configured to communicate a flowable material, stored within the shaft, to the exterior surface, each channel of the one or more channels including an opening at the exterior surface.

7. The dental implant of claim 6, wherein the opening of each of the one or more channels, at the exterior surface, is positioned between successive windings of the at least one thread.

8. The dental implant of claim 6, wherein at least one channel, of the one or more channels, extends between a cavity of the shaft and the exterior surface.

9. The dental implant of claim 8, wherein the at least one channel is oriented at an angle toward the apical end, relative to a plane that is orthogonal to the longitudinal axis, from the cavity to the exterior surface.

10. The dental implant of claim 8, including the flowable material pre-loaded and stored in the cavity.

11. The dental implant of claim 6, including the flowable material pre-loaded and stored in at least one channel, of the one or more channels.

12. The dental implant of claim 6, including the flowable material, the flowable material including at least one of a resorbable polymer, a hydrophilic material, an in-growth promotion material, an insertion aiding material, or an antibiotic.

13. The dental implant of claim 6, including the flowable material, wherein the flowable material includes a powder configured to be hydrated.

14. The dental implant of claim 1, wherein the bone-engaging surface is coated with a material deposited by a chemical vapor deposition process.

15. The dental implant of claim 1, wherein the porous material includes at least one of an organic bone graft, a resorbable polymer, a non-resorbable polymer, a synthetic bone material, tantalum, or collagen.

16. A dental implant, comprising:
a shaft defining a longitudinal axis and having an apical end, a coronal end, an exterior surface, and one or more channels, a portion of the exterior surface including a porous material and each of the one or more channels configured to communicate a flowable material to an opening at the exterior surface;

a non-porous head portion, including a male or female interface for coupling to an abutment, positioned at the coronal end of the shaft; and at least one thread integrally formed with the head portion and the at least one thread and the head portion comprising an initially separate element from the shaft attachable thereto by the head portion, the at least one thread including a non-porous material and having an interior surface and a bone-engaging surface, the interior surface configured to engage and wind around the exterior surface of the shaft to form a porous-non-porous material interface between the interior surface and the exterior surface of the shaft, the bone-engaging surface extending outwardly from the exterior surface of the shaft, wherein the exterior surface of the shaft is exposed.

17. The dental implant of claim 16, wherein at least one of the one or more channels is oriented at a downward angle, relative to a plane that is orthogonal to the longitudinal axis, between an inner portion of the shaft and the exterior surface.

18. The dental implant of claim 17, including the flowable material, wherein the flowable material is configured to flow under gravity when hydrated.

* * * * *